(12) United States Patent
Rek (10) Patent No.: US 8,506,295 B2
(45) Date of Patent: Aug. 13, 2013

(54) FILE FOR WORKING ON THE INTERPROXIMAL SPACE IN ORTHODONTICS AS WELL AS IN CONSERVATIVE TREATMENTS AND PROPHYLAXIS OF TEETH AND RELATIVE DEVICE ABLE TO SEE CONNECTED TO AN OSCILLATING HANDPIECE

(75) Inventor: Peter Rek, Pura (CH)

(73) Assignee: SDC Switzerland SA, Collina d'Oro (CH)

( * ) Notice: Subject to any disclaimer, the term of this patent is extended or adjusted under 35 U.S.C. 154(b) by 36 days.

(21) Appl. No.: 13/202,302

(22) PCT Filed: Feb. 16, 2010

(86) PCT No.: PCT/IB2010/000300
§ 371 (c)(1),
(2), (4) Date: Sep. 28, 2011

(87) PCT Pub. No.: WO2010/095017
PCT Pub. Date: Aug. 26, 2010

(65) Prior Publication Data
US 2012/0148981 A1 Jun. 14, 2012

(30) Foreign Application Priority Data
Feb. 20, 2009 (IT) .............................. MI2009A0239

(51) Int. Cl.
*A61C 3/06* (2006.01)
(52) U.S. Cl.
USPC ......................................................... 433/166
(58) Field of Classification Search
USPC ................... 433/25, 125–127, 141, 142, 146, 433/148, 162, 166, 215, 39; 132/324, 321, 132/329; 606/84, 85
See application file for complete search history.

(56) References Cited

U.S. PATENT DOCUMENTS

| 3,624,908 | A | | 12/1971 | Ricketts et al. | |
| 3,858,368 | A | * | 1/1975 | Cocherell et al. | 451/490 |
| 4,055,897 | A | * | 11/1977 | Brix | 433/166 |
| 4,636,171 | A | * | 1/1987 | Martin | 433/134 |
| RE39,174 | E | * | 7/2006 | Buchanan | 433/102 |
| 7,322,822 | B2 | * | 1/2008 | Navarro | 433/125 |
| 7,455,521 | B2 | * | 11/2008 | Fishburne, Jr. | 433/142 |
| 7,824,182 | B2 | * | 11/2010 | Kim | 433/142 |
| 2005/0058963 | A1 | | 3/2005 | Stockstill | |
| 2006/0057540 | A1 | | 3/2006 | Navarro | |
| 2006/0063131 | A1 | | 3/2006 | Kim | |
| 2008/0213731 | A1 | | 9/2008 | Fishburne | |

FOREIGN PATENT DOCUMENTS

| DE | 34 15 450 A1 | 10/1984 |
| JP | 7 194618 A | 8/1995 |
| WO | 2008/103685 A2 | 8/2008 |

* cited by examiner

*Primary Examiner* — Cris L Rodriguez
*Assistant Examiner* — Matthew Seward
(74) *Attorney, Agent, or Firm* — Kirton McConkie; Evan R. Witt (57) ABSTRACT

A file for working on the interproximal space in orthodontics as well as in conservative treatments and prophylaxis of teeth comprises a tool-holding structure and an abrasive plate, wherein the tool-holding structure is shaped in an arc and provided at the ends with two tubular portions and wherein the abrasive plate is stably fixed at both of its ends to the tubular portions of the tool-holding structure, wherein the tool-holding structure is symmetrical and overmolded on said abrasive plate. A relative device able to be connected to an oscillating handpiece comprises such a file and a shank for the connection to the handpiece, wherein the shank is removably fixed to the file.

18 Claims, 7 Drawing Sheets

FILE FOR WORKING ON THE INTERPROXIMAL SPACE IN ORTHODONTICS AS WELL AS IN CONSERVATIVE TREATMENTS AND PROPHYLAXIS OF TEETH AND RELATIVE DEVICE ABLE TO SEE CONNECTED TO AN OSCILLATING HANDPIECE

The present invention refers to a file for working on the interproximal space in orthodontics as well as in conservative treatments and prophylaxis of teeth and to a relative device able to be connected to an oscillating handpiece.

Dental files for orthodontics are known to be used comprising an abrasive working portion and a handle able to be connected to an oscillating handpiece, so called EVA, like those used by dentists.

Such files are used for so called "stripping", i.e. to reduce the structure of a tooth through the removal of small quantities of enamel. This treatment makes it possible to widen the interproximal space between two teeth that are too close to one another and to avoid having to extract a tooth.

Known dental files comprise a support structure made from synthetic material and a thin diamond-tipped stainless steel plate, in which the abrasive plate is fixedly attached, at one or both ends, to the support structure that connects it to the oscillating handpiece. Preferably, one or more ends of the abrasive metal plate are embedded in the handle in the molding step.

According to a further known embodiment, the dental file comprises a stainless steel frame in one piece, which makes up both the abrasive working portion and the handle. In particular, in the abrasive working portion, the metallic frame is diamond-tipped and at the handle it is covered with plastic material.

According to what is known, the abrasive plate can be provided with small holes distributed on the surface so as to facilitate the discharge of the enamel removed from the tooth.

A file according to the teachings of U.S. Pat. No. 3,624,908 is provided with a support structure of the abrasive plate, comprising an arc portion and an end appendix, in which the end appendix is screwed onto the shank in turn able to be connected to an oscillating handpiece.

The dental files described must be able to be used on both their faces, for treating, for example, opposing surfaces of two adjacent teeth. They are thus equipped with abrasive material on both sides of the plate, or they are made in two different models, right-handed and left-handed, each provided with the abrasive material on an opposite side.

Moreover, different types of files are made with a granulometry of the abrasive material which is variable based upon the type of treatment to be carried out and upon the interproximal space available for the file to be inserted into. Also the type of abrasive surface can be different based upon its intended use.

Consequently, during the orthodontic treatment on a patient, many different files are generally used, said files having to be applied to the handpiece and then removed each time. The assembly of the file to the handpiece constitutes an operation that has substantial drawbacks, since the handpieces currently used and on the market do not have standard tool insertion hole sizes. Even small differences in the diameter cause a loose assembly of the file or difficulty inserting a file with a handle which is too big with respect to the hole of the handpiece, which also carries the risk of damaging it.

The application of a file to a handpiece is thus a critical operation that requires time and concentration.

A further drawback of current dental files consists of the need, due to the above, to use a great number of different files. Consequently, the supplies are costly for the user and there are higher production and warehouse management costs for the manufacturer.

The purpose of the present invention is that of making a file, for working on the interproximal space in orthodontics as well as in conservative treatments and prophylaxis of teeth, that is rapidly interchangeable.

Another purpose of the present invention is that of making a file for working on the interproximal space and a relative device able to be connected to an oscillating handpiece that achieve a higher level of standardization of the components.

Another purpose of the present invention is that of making a file for working on the interproximal space in orthodontics as well as in conservative treatments and prophylaxis of teeth and a relative device able to be connected to an oscillating handpiece which are particularly simple and functional, and have low costs.

These purposes according to the present invention are achieved by making a file for working on the interproximal space and a relative device able to be connected to an oscillating handpiece as outlined in claim 1.

Further characteristics are provided in the dependent claims.

The characteristics and the advantages of a file for working on the interproximal space in orthodontics as well as in conservative treatments and prophylaxis of teeth and of a relative device able to be connected to an oscillating handpiece according to the present invention shall become clearer from the following description, given as an example and not for limiting purposes, with reference to the attached schematic drawings, in which:

FIG. 10 shows a further shank for a device for working on the interproximal space according to the invention;

FIG. 11 is a perspective view of a further embodiment of a file for working on the interproximal space according to the invention provided with an abrasive plate with double thickness;

FIG. 12 shows a device for working on the interproximal space provided with an abrasive plate with a smooth entry portion with a lower height;

FIGS. from 13 to 16 show a device for working on the interproximal space in which the abrasive plate is made with different abrasive surfaces, with or without diamonds, for prophylaxis.

With reference to the figures, a file for working on the interproximal space in orthodontics as well as in conservative treatments and prophylaxis of teeth is shown wholly indicated with reference numeral 10 (FIGS. 1-3 and 11), as well as a relative device 100 able to be connected to an oscillating handpiece comprising the file 10 (in FIGS. 4A-4C, 8, 9 and 12-16) and a shank 20 (FIGS. 5-7 and 10).

The file 10 according to the invention comprises an abrasive plate 11 and a tool-holding structure 12, stably fixed to the abrasive plate 11.

The tool-holding structure 12, according to the invention, is symmetrical and arc-shaped. At the ends of the arc, it is provided with two tubular portions 13 and 13', having their axis X parallel to one another and lying on the plane of the abrasive plate 11.

The abrasive plate 11 is stably fixed, at both of its opposite ends, to the tubular portions 13 and 13' of the tool-holding structure 12.

In particular the tool-holding structure 12, generally made through molding in synthetic material, such as polyamide (PA) or synthetic material combined with carbon fibers (LCP), is overmolded on the abrasive plate 11.

The abrasive plate 11 can be a plate of stainless steel with a portion provided with abrasive material 14, in particular diamond-tipped, or it can be an abrasive plate of an innovative type comprising a sheet of polyester on which abrasive material 14, such as aluminum oxide is glued, at least on one side.

Figure 4A:
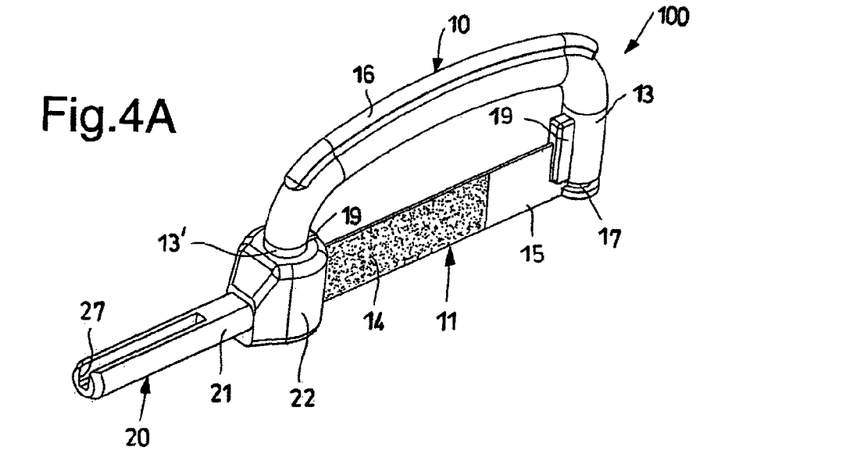
FIGS. 4A, 4B are perspective views of a first embodiment of a device for working on the interproximal space according to the invention, comprising the file of FIG. 1.
Figure 4B:
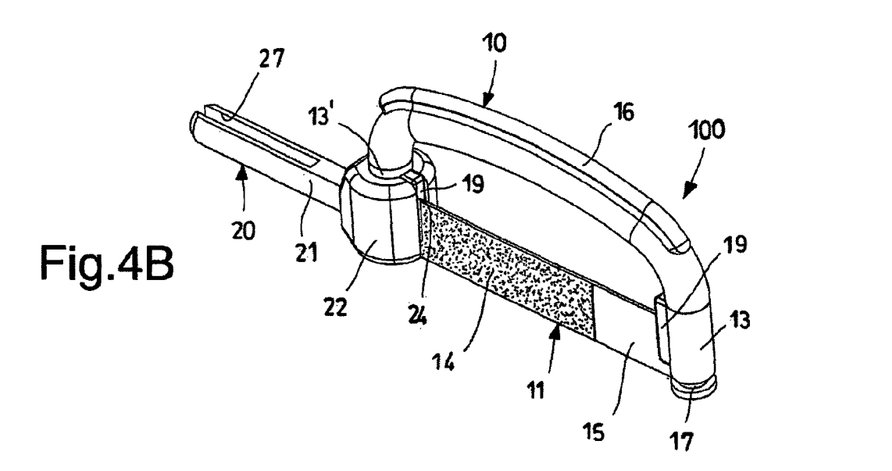
Figure 4C:
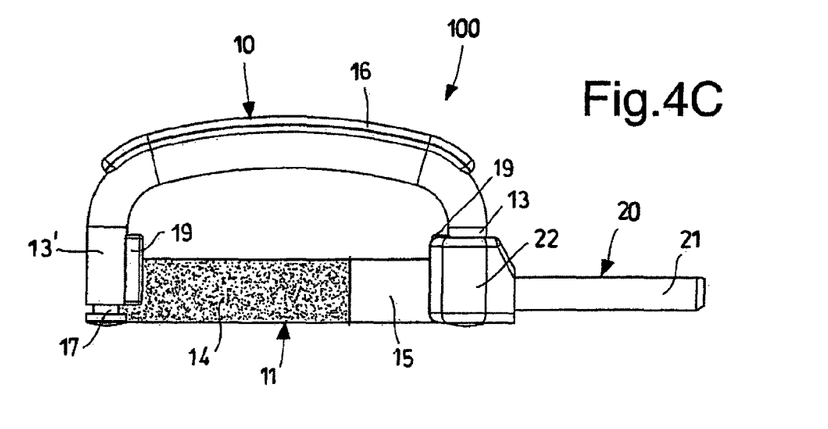
FIG. 4C is an elevational side view of the device of FIGS. 4A and 4B, in which a shank is connected to the opposite end.

Moreover, preferably, the abrasive plate 11 comprises at least one smooth entry portion 15, i.e. without abrasive material 14 near to an end (FIGS. 4A-4C).

Figures 10, 11, 12, 13, 14, 15, 16:
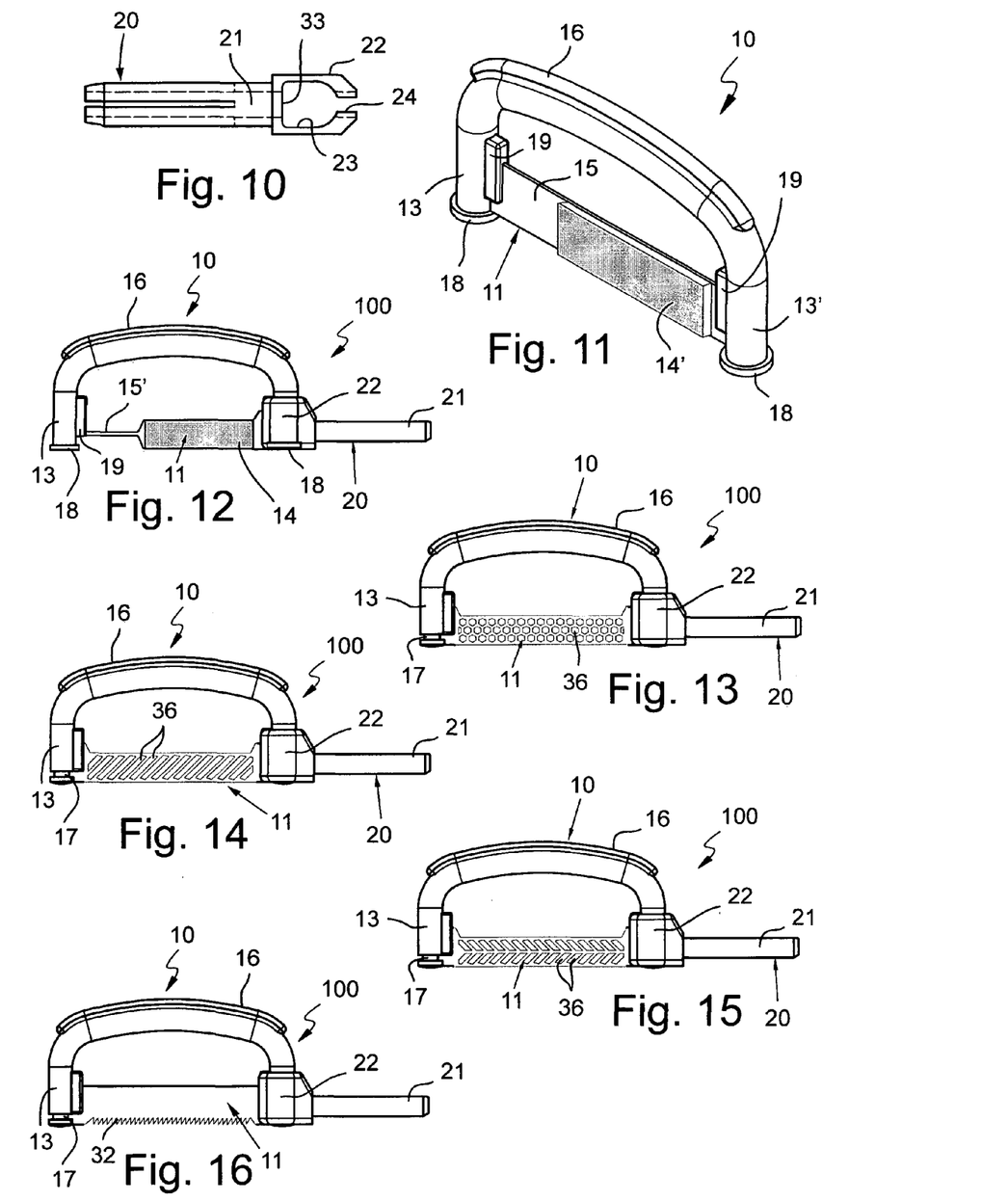

Advantageously, the smooth entry portion 15 can be extended up to about one third of the overall length of the abrasive plate 11 (FIGS. 11 and 12).

Figure 1:
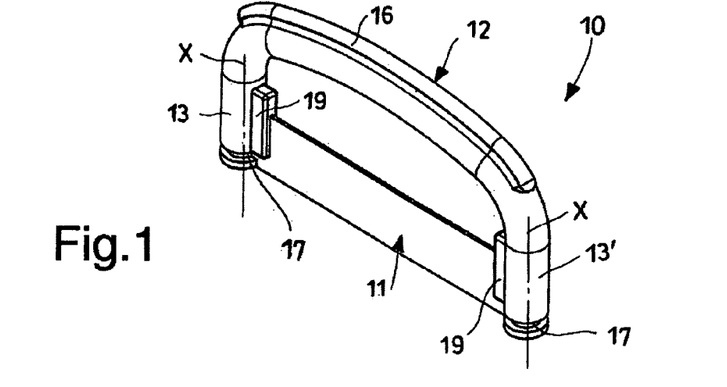
FIGS. 1-3 are perspective views of different embodiments of a file for working on the interproximal space according to the invention.

FIGS. 1 and 4 show the same file 10, on the side which is not coated with abrasive material (FIG. 1) and on the side coated with abrasive material 14, respectively, and it is provided with a smooth entry portion 15 (FIG. 4).

Such an abrasive plate made from polyester can be used, according to the invention, in any type of file, even with a shank for the connection to a handpiece fixedly connected to it.

The abrasive plate made from polyester is thinner and has a finer grain with respect to conventional diamond-tipped stainless steel plates. This allows files to be made which are suitable for being inserted into an interproximal space between due adjacent teeth. Finishing operations, which remove less material from the surface of the tooth, can also be carried out through the abrasive plates made from polyester.

This makes it possible to use files with abrasive plates made from polyester even in so called "conservative" treatments, in which finishing and polishing of synthetic dental crowns are carried out.

As shown for example in FIG. 11, the file according to the invention can comprise an abrasive plate 11 consisting of a diamond-tipped stainless steel metallic plate in which the smooth entry portion 15 is thinner than the diamond-tipped abrasive portion 14. The thicker part is made in one piece with the smooth portion having a smaller diameter and it can take on values from 0.2 mm to 0.5 mm. The provision of a diamond-tipped portion with greater thickness 14' makes it possible for the plate to be diamond-tipped with fine grains instead of with coarse grains so as to avoid indentations on the enamel and to improve the surface and the quality of the treatment.

Moreover, the abrasive metallic plate 11, as shown in FIG. 12, can have a smooth entry portion with a lower height 15' with respect to the abrasive portion 14. This makes it easier for the file to be inserted between two teeth through a more rapid introduction of the file without scraping at the point of contact.

The smooth entry portion with lower height 15' can have a height of between 0.5 mm and 1 mm and thus substantially shorter with respect to the height of at least 2.5 mm of the diamond-tipped portion 14. This configuration allows the abrasive plate 11 to adapt to the shape of the tooth in the filing step to avoid undesired indentations from forming.

FIGS. from 13 to 15 show some possible embodiments of abrasive plates 11 for the prophylaxis, i.e. to remove the interdental plaque without etching the enamel. These files comprise a metallic plate provided with a plurality of holes 36 distributed uniformly over all or at least part of the surface. The abrasive plate 11 can be with or without diamonds. The different diamond-tips and the different configurations of the holes 36 are selected based upon the requirements, and in particular, to remove the plaque from the enamel of the teeth in the interproximal areas.

FIG. 16 also shows an abrasive plate provided with a serration 32 to open the interproximal contact point between two teeth. The abrasive plate 11 is preferably not diamond-tipped when provided with a serration 32 on the lower side.

Figure 3:
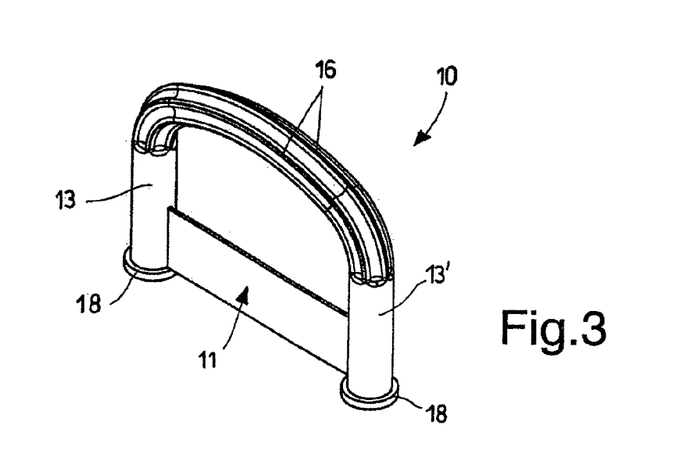

Moreover, in the file 10 according to the present invention, the tool-holding structure 12 can be provided, in a preferred embodiment, with stiffening means 16 for the arc, for example consisting of a more or less extended projection (FIG. 1) or by a plurality of crests and valleys (FIG. 3).

Another object of the present invention is the relative device 100 for working on a surface of a tooth able to be connected to an oscillating handpiece, so called EVA handpiece, FIGS. 4A-4C and 8-9, comprising the aforementioned file 10 and the shank 20 for the connection to the handpiece, not shown, in which the shank 20 is removably fixed to the file 10.

Thanks to the possibility of removing the shank 20 from the file 10, according to the invention, the abrasive plate 11, both of metal and polyester, can be equipped with abrasive material 14 even on only one side, instead of on both, whilst still allowing it however to be used both as a right-handed file or as a left-handed file. Indeed, by applying the shank 20 to the first tubular portion 13' (FIGS. 4A and 4B) rather than to the opposite tubular portion 13 (FIG. 4C), the same file 10 can be right-handed or left-handed.

The shank 20 comprises an elastic tang 21 for the connection to the handpiece and a gripping head 22 extending in one piece at an end of the tang 21 for engagement with any one of the tubular portions 13, 13' of the tool-holding structure 12 of the file 10.

In particular, the gripping head 22 and the tubular portions 13, 13' of the tool-holding structure 12 comprise a plurality of matching stable coupling means. Indeed, both the rotation and the relative translation between the file 10 and the shank 20 must be prevented.

Figure 5A:
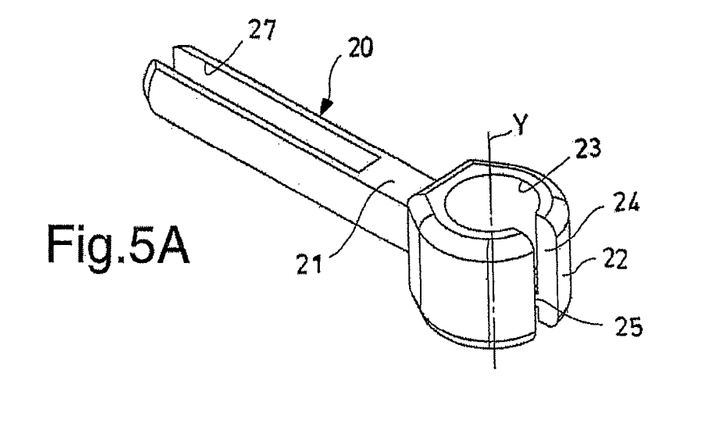
FIG. 5A is a perspective view of the shank of FIG. 4.
Figure 5B:
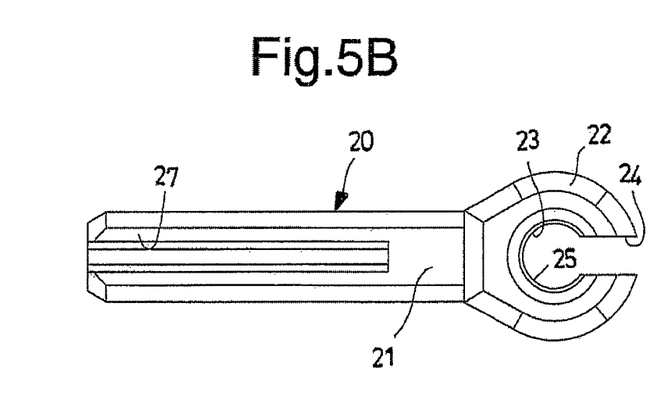
FIG. 5B is a plan view of the shank of FIG. 5A.
Figure 5C:
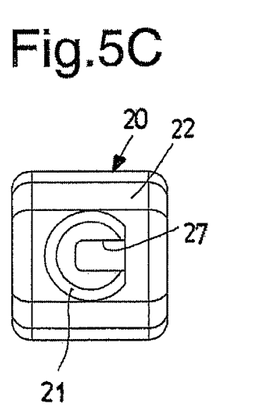
FIGS. 5C and 5D are elevational views of the shank of FIG. 5A.
Figure 5D:
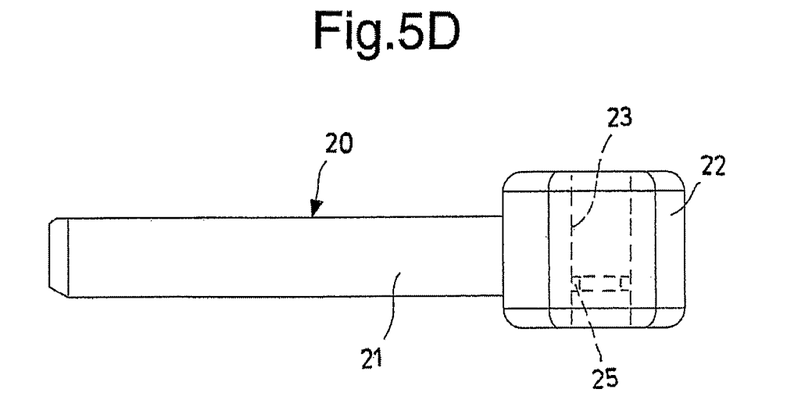

The stable coupling means comprise the tubular portions 13, 13' of the tool-holding structure 12 that engage with a matching tubular seat 23 of the gripping head 22 having axis Y perpendicular to the tang 21, as shown in FIG. 5A. The matching tubular seat 23 guides the insertion of any one of the tubular portions 13 or 13' of the file 10 along the direction defined by the axis Y of the tubular seat 23. The tubular seat 23 also comprises a longitudinal notch 24 opposite the tang 21 that receives the abrasive plate 11 in its assembled position with a perfect fit.

The tubular seat 23 can have a circular section or another section, for example it can be provided with at least one flat wall 33 (FIG. 10) that gives further stability to the rotation. The walls of the tubular seat 23 are in any case all parallel to the axis Y.

Other stable coupling means comprise at least one annular recess 17 and an annular ridge 25, matching one another, arranged perpendicular to the axis Y of the tubular seat 23 and to the axis X of the tubular portions 13, 13' for an axial snap engagement between file 10 and shank 20.

In most of the examples shown, given as an example and not for limiting purposes, the tubular portions 13, 13' of the file 10 are provided with the annular recess 17 and the tubular seat 23 of the shank 20 is provided with the annular ridge 25 (FIGS. 1, 2, 4 and 5). According to the invention, the position of recesses and projections could be reversed in a completely equivalent manner, foreseeing an annular ridge 18 on the file 10 (FIG. 3) and a matching recess 31 on the shank 20, shown in FIGS. 8 and 9.

Moreover, the stable coupling means can comprise at least one longitudinal rib 19 in a symmetrical position on both the tubular portions 13, 13' that makes the anti-rotational coupling with matching portions of the gripping head 22.

According to a first preferred embodiment, the ribs 19 are arranged near to the ends of the abrasive plate 11 and are suitable for coupling with the longitudinal notch 24 of the shank 20.

Figure 2:
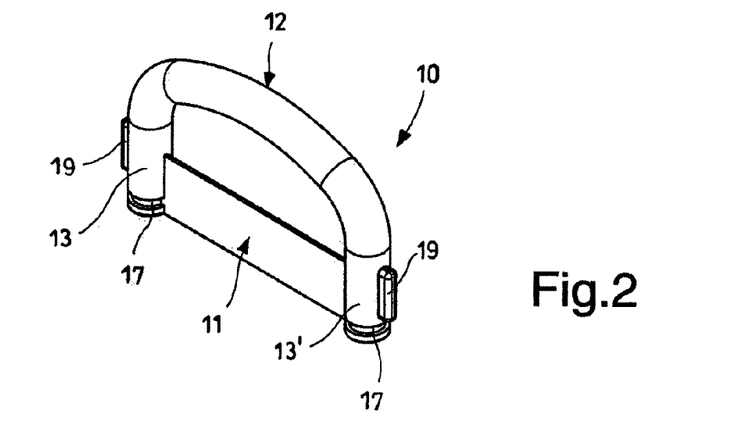
Figure 6:
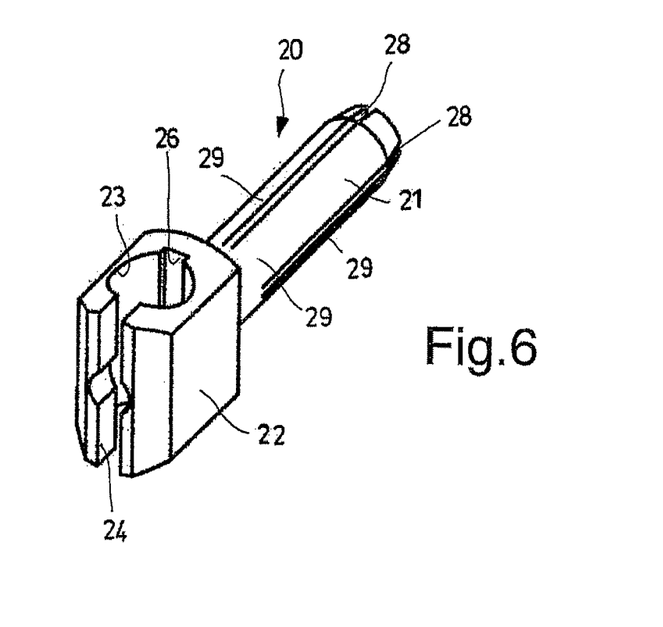
FIGS. 6 and 7 are perspective views of further embodiments of the shank for a device for working on the interproximal space according to the invention.

In a second embodiment shown in FIG. 2, the rib 19 is positioned on the tubular portion 13, 13' on the side opposite with respect to the abrasive plate 11 and it is suitable for coupling with at least one matching longitudinal groove 26, made on the inner surface of the tubular seat 23, as shown in FIG. 6.

Figure 7:
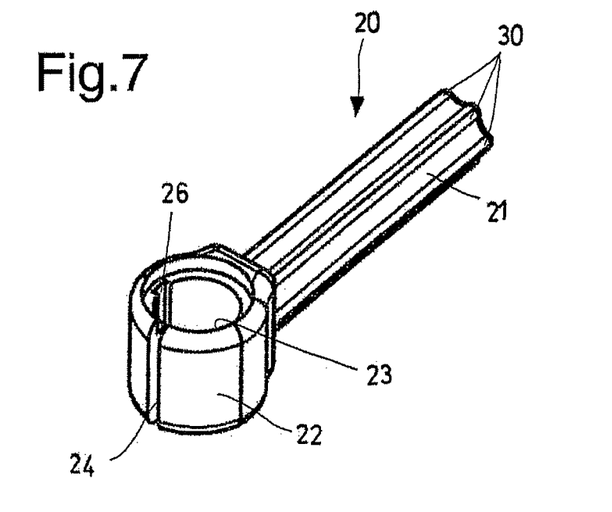

Alternatively, there can be also many longitudinal ribs 19 for each tubular portion 13, 13', for example two opposite ribs 19 perpendicular with respect to the abrasive plate 11, that engage with relative longitudinal grooves 26 of the tubular seat 23 (FIG. 7).

Figure 8:
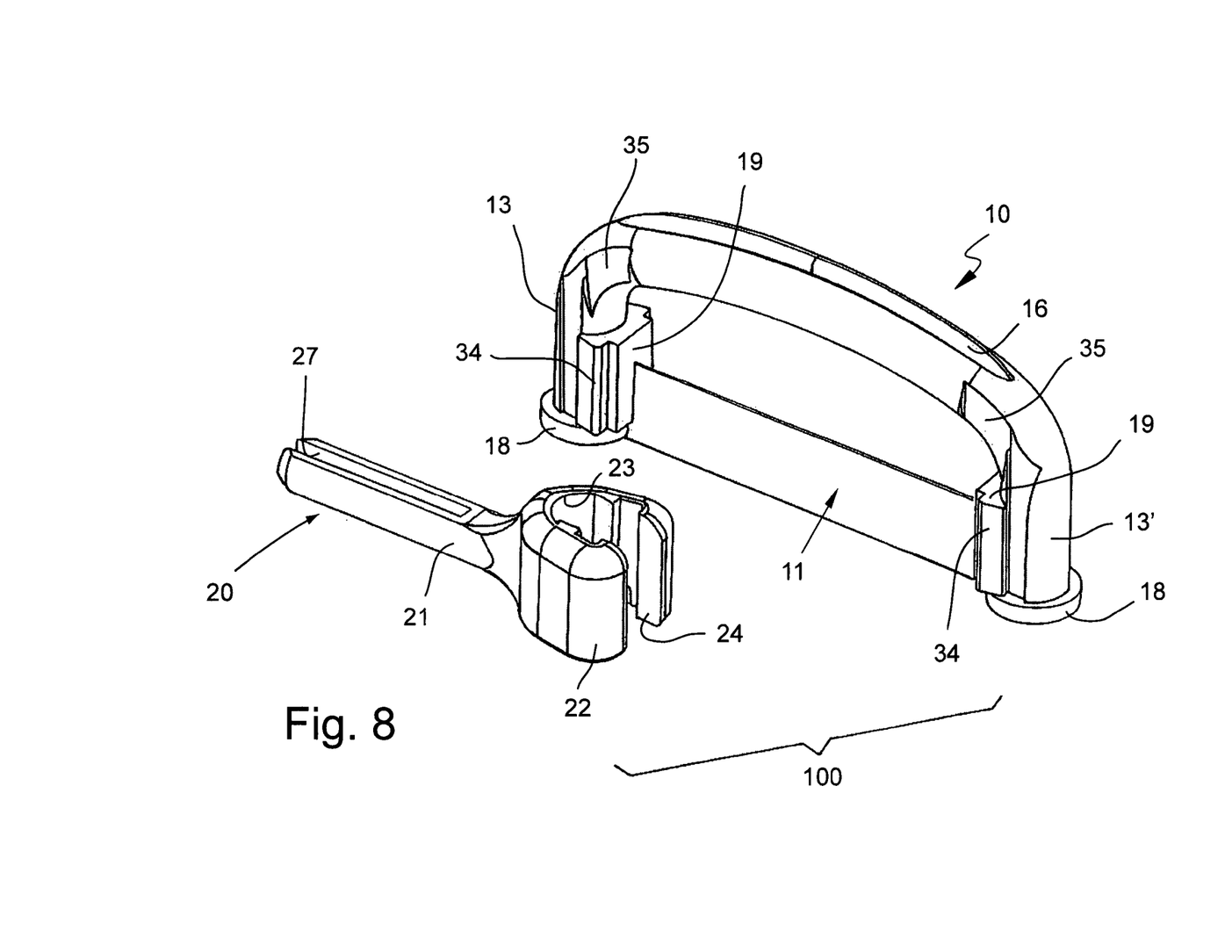
FIGS. 8 and 9 are two exploded views of a further embodiment of a device for working on the interproximal space according to the invention.
Figure 9:
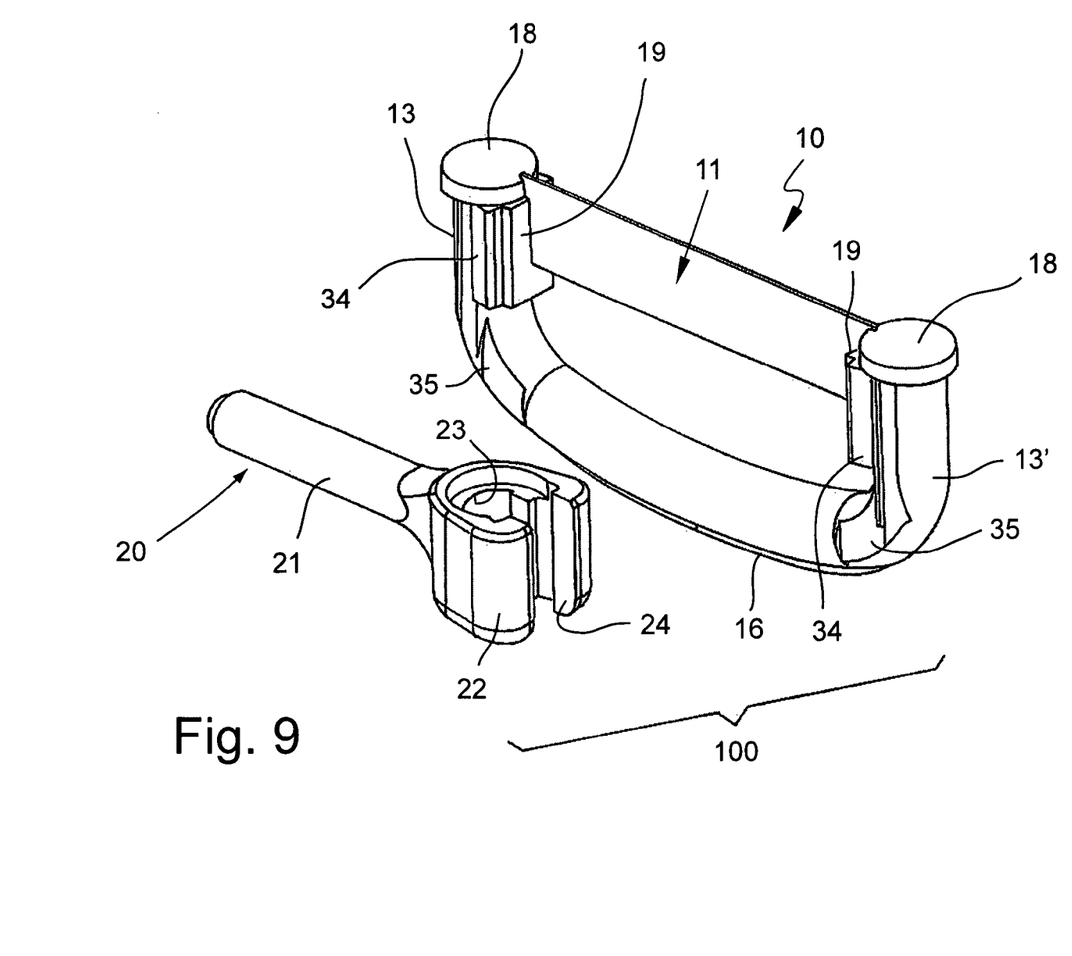

According to a further embodiment, shown in FIGS. 8 and 9, the tubular portions 13, 13' further comprise a succession of ribs and grooves, to identify a broken profile 34 for coupling with matching portions of the gripping head (22).

In the example shown, the file 10 also comprises flattened side portions 35 to allow the gripping head 22 of the shank 20 to be inserted.

Moreover, in the shank 20 of FIG. 7, the notch 24 is thinner and equal to the thickness of the abrasive plate 11.

The shank 20 of the device for working on a surface of a tooth according to the invention 100 can be provided with different elastic tangs 21.

In FIGS. 5A-5D, the tang 21 has a longitudinal groove 27 that allows a certain deformation during the insertion into the handpiece.

FIG. 6, on the other hand, shows a tang 21 provided with a plurality of longitudinal notches 28 that identify flexible portions of wall 29. Such a tang can have a slightly greater diameter with respect to the hole of the resting handpiece and it can be compressed while being inserted.

The shank 20 shown in FIG. 6, is provided with a tang 21 comprising the flexible portions of wall 29, which can be made in metallic material.

A further embodiment of the elastic tang 21 is shown in FIG. 7 and foresees there to be a plurality of longitudinal crests 30 arranged on the entire perimeter of the tang 21 so as to form an undulated profile able to deform if necessary for the insertion into the handpiece.

The file for working on the interproximal space in orthodontics as well as in conservative treatments and prophylaxis of teeth object of the present invention has the advantage of being able to be used, without distinction, as a right-handed file or left-handed file without requiring different right and left-handed models to be made.

The relative device able to be connected to an oscillating handpiece, object of the invention, has the advantage of being partially removable from the handpiece in a short time and of being more easily adapted to all different handpieces present on the market.

The file according to the invention can advantageously be used also manually in an effective manner.

The file for working on the interproximal space in orthodontics as well as in conservative treatments and prophylaxis of teeth, and the relative device able to be connected to an oscillating handpiece, thus conceived can undergo numerous modifications and variants, all covered by the invention; moreover, all the details can be replaced by technically equivalent elements. In practice, the materials used, as well as the sizes, can be any according to the technical requirements.

The invention claimed is:

1. A device for working on an interproximal space in orthodontics, in conservative treatments, and prophylaxis of teeth, able to be connected to an oscillating handpiece, the device comprising a file having a tool-holding structure and an abrasive plate, wherein said tool-holding structure is shaped in an arc and provided at ends of said tool-holding structure with two tubular portions, wherein said abrasive plate is stably fixed at both ends of said abrasive plate to said tubular portions of said tool-holding structure, said tool-holding structure being symmetrical and overmolded on said abrasive plate, and a shank for the connection to said handpiece, said shank being removably fixed to said file alternatively at any selected one of said two tubular portions, wherein said shank comprises an elastic tang for the connection to said handpiece and a gripping head extending in one piece at an end of said tang for engagement with any one of the ends of said tool-holding structure of said file, wherein said gripping head and said tubular portions of the tool-holding structure comprise a plurality of matching stable coupling means, and wherein said stable coupling means comprise said tubular portions of the tool-holding structure and a matching tubular seat of the gripping head having a vertical axis perpendicular to the tang, said matching tubular seat comprising a longitudinal notch in a position opposite said tang and being suitable for guiding the insertion of any one of said tubular portions of the file along the direction defined by the axis of the tubular seat, said stable coupling means comprising at least one annular recess and an annular ridge, matching one another, arranged perpendicular to the vertical axis of the tubular seat and to a horizontal axis of the tubular portions for an axial snap engagement.

2. The device according to claim 1, characterized in that said stable coupling means further comprise, on both the tubular portions, at least one anti-rotation longitudinal rib, for coupling with matching portions of said gripping head.

3. The device according to claim 2, characterized in that said anti-rotation longitudinal ribs are arranged near to the ends of the abrasive plate and are suitable for coupling with said longitudinal notch.

4. The device according to claim 2, characterized in that said anti-rotation longitudinal ribs are separate with respect to said plate and are suitable for coupling with at least one matching longitudinal groove made on the inner surface of said tubular seat.

5. The device according to claim 2, characterized in that said tubular portions further comprise a succession of ribs and grooves, to form a broken profile for coupling with matching portions of said gripping head.

6. The device according to claim 2, characterized in that said tubular portions have at least one flat wall.

7. The device according to claim 2, characterized in that said tang has at least one longitudinal groove.

8. The device according to claim 1, characterized in that said tang has a plurality of longitudinal crests.

9. The device according to claim 1, characterized in that said tang comprises a plurality of longitudinal notches that form flexible wall portions.

10. The device according to claim 9, characterized in that said shank is made from metallic material.

11. The device according to claim 1, characterized in that said abrasive plate comprises at least one smooth entry portion near to one of the ends of said abrasive plate.

12. The device according to claim 11, characterized in that said smooth entry portion extends along at least one third of the length of said abrasive plate.

13. The device according to claim 11, characterized in that said abrasive plate comprises a metallic plate comprising a smooth entry portion with a lower height with respect to said abrasive portion.

14. The device according to claim 11, characterized in that said abrasive plate comprises a metallic plate and a diamond-tipped abrasive portion, wherein said diamond-tipped abrasive portion has a greater thickness with respect to said smooth entry portion.

15. The device according to claim 1, characterized in that said abrasive plate is provided with a plurality of holes distributed uniformly on at least part of a surface of said abrasive plate, said abrasive plate being with or without diamonds.

16. The device according to claim 11, characterized in that said abrasive plate comprises a sheet of polyester on which abrasive material is glued on at least one side.

17. The device according to claim 1, characterized in that said tool-holding structure is provided with stiffening means for the arc.

18. The device according to claim 16, characterized in that said abrasive plate comprises a sheet of polyester, on which, at least on one side and at least in a central area, abrasive material is glued.

* * * * *